(12) United States Patent
Kasper et al.

(10) Patent No.: US 7,819,526 B2
(45) Date of Patent: Oct. 26, 2010

(54) FUNDUS CAMERA

(75) Inventors: Axel Kasper, Munich (DE); John Robert Zinter, Rochester, NY (US)

(73) Assignee: Linos Photonics GmbH & Co. KG, Goettingen (DE)

( * ) Notice: Subject to any disclaimer, the term of this patent is extended or adjusted under 35 U.S.C. 154(b) by 30 days.

(21) Appl. No.: 12/150,420

(22) Filed: Apr. 28, 2008

(65) Prior Publication Data
US 2008/0278686 A1 Nov. 13, 2008

(30) Foreign Application Priority Data
May 18, 2007 (DE) .................. 10 2007 023 270

(51) Int. Cl.
*A61B 3/10* (2006.01)
(52) U.S. Cl. .................. 351/211; 351/221; 351/206; 351/215
(58) Field of Classification Search .................. 351/211, 351/221
See application file for complete search history.

(56) References Cited

U.S. PATENT DOCUMENTS
7,115,848 B1  10/2006  Zinter et al.

FOREIGN PATENT DOCUMENTS
CA    2284299      3/2001
WO    WO 98/45745  10/1998

*Primary Examiner*—Jessica T Stultz
(74) *Attorney, Agent, or Firm*—Karl F. Milde, Jr.; Eckert Seamans Cherin & Mellott, LLC

(57) ABSTRACT

The components of a fundus camera for observing an eye (11)—namely, an illumination device (1) to illuminate an image field of the eyeground (12) and an image recording device (14) onto which the eyeground (12) is projected by means of a projection device (10)—are positioned to be confocal. The illumination device (1) is so structured that a periodic light pattern is created against the eyeground (12) within the illuminated image field. Further, an offset medium is present to offset the pattern by less than one period. The image recording device (14) is connected to an evaluation unit (22) in order to combine at least three recordings illuminated with offset patterns into a single photograph. A single, unstructured, extremely sharply focused photograph of the eyeground (12) may thus be obtained.

24 Claims, 2 Drawing Sheets

FUNDUS CAMERA

BACKGROUND OF THE INVENTION

The invention relates to a so-called "fundus camera" for recording an image of the retina in the background of an eye; that is, the "eyeground" or "fundus" of an eye.

Two different procedures are known for the observation of the eyeground.

In the conventional procedure, the eyeground is illuminated using a beam emitted from a light source, and an image is conducted to a sensor by means of an intermediary image using the light reflected or emitted there. This procedure admits of the difficulty that the illumination and the observation must be performed through the iris upon which reflections occur that create image errors.

This procedure was considerably improved by positioning the light source and the detector so that the excitation focus and detector focus were confocal. Thus, optical information coming from other than the focal plane may be easily suppressed, which clearly improves the image quality of the photographs. However, even this result is inadequate to provide some fine details of the eyeground.

Another procedure was therefore developed in which the eyeground is not illuminated completely to its edge, but rather is sampled using a focused light beam and the reflected light is collected by a sensor with a sampling frequency assigned to it. Devices used to obtain this fundus image are called Scanning Laser Opthalmoscopes or Retinal Scanners. A disadvantage of this procedure is that the system required is relatively complex and expensive, and that a time delay arises because of the point-for-point sampling which, in particular, leads to false results because of eye movements. In order to deal with this problem, a wide variety of suggestions have been proposed, each of which causes the system to become more expensive.

SUMMARY OF THE INVENTION

It is the principal objective of the present invention to develop a fundus camera that is inexpensive to manufacture but simultaneously creates high-quality images of the eyeground.

This objective, as well as other objectives which will become apparent from the discussion that follows, are achieved, in a fundus camera of the type wherein excitation focus of the illumination device and the detector focus of the image recording device are confocal. In accordance with the invention, the illumination device is so structured that a periodic light pattern is created against the eyeground within the illuminated image field. Further, an offset medium is present to offset the pattern by less than one period. The image recording device is connected to an evaluation unit in order to combine at least three recordings illuminated with offset patterns into a single photograph. A single, unstructured, extremely sharply focused photograph of the eyeground is thus obtained.

Based on the invention, a fundus camera that takes a planar photograph is equipped with patterned illumination. A periodic light-intensity pattern, or a repeating series of light-dark transitions is created against the eyeground because of the patterned illumination. This series only creates a sharp image in the focal plane of the image-photographing device that corresponds to the focal plane of the illumination device. The structures of the eyeground that lie exactly in the focal plane of the illumination device include in the photograph a modulation of the image signal that corresponds to the illumination pattern. Structures that lie at another depth produce considerably less modulation of the image signal in the photograph. Only weakly modulated signals that do not originate from the focal plane are thus overlaid onto the completely modulated image from the focal plane of the illumination device.

In order to clean up a photograph and to convert into a photograph in which, first, the illumination pattern is no longer visible, and second, all image signals that do not originate from the focal plane are eliminated, at least two additional flat photographs are created while maintaining the focus, in which the patterned illumination is so altered that the periodic light pattern is offset by less than one period with respect to the previous photograph. In an advantageous embodiment of the invention, the offset is equidistant and the displacement path for n partial photographs corresponds exactly to one $n^{th}$ of the period of the illumination pattern. If this minimum of three photographs created with offset structure are calculated together, all interference signals may be removed from the photograph and subsequently a full-surface, extremely sharp, high resolution photograph of a plane of the eyeground may be derived that formerly could only be achieved using a retinal scanner. A procedure to process the individual photographs into a corrected combined photograph is known, for example, from the European Patent No. EP 0 972 220 B1. With this expansion based on the invention, photograph quality may be achieved while maintaining the design of a classical fundus camera that is inexpensive to manufacture, quick, and efficient for surface sampling that otherwise is possible only using the vastly more expensive and inconvenient optics of a retinal scanner. For this, merely a modification of the illumination unit, a photograph, and evaluation of several photographs is required. Modification of the illumination to create the periodic illumination pattern may be realized using widely varying illuminations. Thus, first, a planar light source before which a grid is positioned may be used. Other light relays such as, for example, LCD arrays or OLED displays may be used advantageously, onto which the illumination pattern may be created directly. An interferometer may also be used advantageously as an illumination device in order to create a periodic stripe pattern by means of interference of coherent beams that then is formed on the retina as patterned illumination.

An essential aspect of the invention related to the use within a fundus camera is the fact that the eye may be moved during the photograph. Thus, the illumination device must be so configured that the offset of the pattern may occur during the extremely brief time interval of less than a half second. This ensures that the minimum of three individual photographs that are combined into a single photograph within the time interval of a second may be recorded. It is even more advantageous if the offset time may be reduced to less than 0.1 second so that the photograph exposure time of the three photographs to be combined is less than 0.2 second. This can almost completely exclude the possibility that eye movement during the photograph exposures provide a false result. Since the three photographs to be combined are exposed within a brief time, it is possible to realize an algorithm as proposed for a fundus camera in the aforementioned EP 0 972 220 B1.

In an advantageous embodiment, the periodic light pattern may be created on the eyeground in that a mask, a grid, or a filter is positioned within the illumination-beam path. This structuring element is advantageously displaced between the photographs by means of a device within the beam path. This device may, for example, be a piezo-actuator or magnetostrictive actuator. Such devices are inexpensive and reliable. It would also be conceivable for the illumination source to possess a periodic pattern and the entire light source may be displaced using an actuator. Such a device generally fulfills the requirements for the necessary rapid displacement.

In a particularly advantageous embodiment, eye movement, which was identified as a problem in the previous example, is used to advantage. During eye movement, the illumination pattern moves against the eyeground. Thus, any additional movement of the illumination pattern may be suspended if the movement of the eyeground is either concretely controlled or at least completed, or an algorithm to evaluate the images may operate with random movement. All advantages of the use of patterned illumination may be achieved by means of a static illumination structure within the fundus camera in that movement of the illumination is used instead of the movement of the object (here, of the eye). This unique advantage results first from the use of patterned illumination within a fundus camera, and was first known here. In particular, eye movement is very rapid, so that with this version, a particularly rapid series of several photographs is possible, thus making almost real-time evaluations possible.

Thus, eye movement may often be so controlled by means of specific movement of one of the fixation targets which are often included within the fundus camera such that the illumination structure follows the fixation target about the eyeground resulting in specific established paths. These are also as known, so that during displacement of the illumination structure itself, it may easily be taken into account during evaluation. For this, the evaluation is communicated regarding the extent to which the fixation target was displaced. The movement of the fixation target may thus advantageously result virtually by altering the display of a light relay such as, for example of a display or LED array, representing a target.

In a further advantageous embodiment, random eye movement is permitted but is recorded or determined from the image data of the photograph. Edge-detection processes or other known algorithms from image processing, for example, may be used to determine the displacement vector. For this embodiment example, a static illumination source is required as a modification of the fundus camera and an evaluation unit that can process a series of photographed images taking their displacement into account.

In an advantageous embodiment, the image recording device possesses resolution of at least one mega-pixel. Only the use of such high resolution can ensure that adequate detail resolution of the photograph required for a diagnosis may be achieved while simultaneously providing a photographed area of the eyeground that is adequate for an overview using a single photograph. Only such high resolution ensures that detail accuracy and sharp focus achieved using patterned illumination may be realized.

In a further advantageous embodiment of the invention, elements and/or configurations of elements are provided that suppress the reflections of the illumination light, which as interference beams may seriously detract the quality of the photograph. In general, one begins with the procedure disclosed in the aforementioned European Patent No. EP 0 972 220 B1 wherein image information not coming from the focal plane is automatically suppressed and has no influence on photograph quality. If this form of patterned illumination is used in a fundus camera, then this assumption that surprisingly arose cannot be maintained. There is the problem within a fundus camera that the useful signal reflected from the eyeground, which represents the actual image to be recorded is extremely weak with respect to the overall signal caused by reflections within the eye, for example. It has therefore been recommended by the invention to employ another measure in order to filter out only that weak signal of the light reflected from the retina being observed. This allows even more improvement to images quality.

Polarizers are advantageously positioned between the light source and the object being photographed, and between the object and the photograph-recording device, whereby the polarizers are orthogonal with respect to each other (so-called crossed polarizers). Polarizers with a very high degree of polarization are preferred. This takes advantage of the fact that the reflection or back-scattering onto the retina acts as a de-polarizer to the light to be recorded, while this does not apply to many other interfering reflections (e.g., from lens surfaces of the optical system or from the cornea).

In order to increase the level of transmission effectiveness for the light to be used, it is advantageous to implement as a polarizer a beam splitter that conventionally is used in confocal cameras in order to separate illumination and recording beam path.

However, a disadvantage in the use of polarizers is the fact that they absorb a major component of the light passing through them. It is therefore provided in an additional advantageous embodiment to position one, several, or all lenses as de-centered and tipped within the beam path used both by illumination and observation together. Thus, undesired reflections from the illumination do not reach the recording sensor, but rather are absorbed at suitable locations within the optical configuration.

With the configuration based on the invention, it is possible and advantageous to conduct a high-resolution depth scan of the eyeground in that an optical element is positioned within the illumination and observation beam path that is so constructed that, with the help of this element, the focal plane may be displaced on the eyeground to be recorded. This may be realized by means of a moveable lens, or also, for example, by means of an active optical element whose diffraction power may be altered. Since the focus is spatially displaced, the depth of the eyeground is sampled, whereby at each new focal position at least three recordings are to be made that then are combined into a single photograph.

In another advantageous embodiment, the evaluation device is so equipped that the recordings made at various focal planes are examined for the characteristic properties that are to be found on all these recordings. Thus, a spatial assignment of the images may be performed, and thereby displacements caused by eye movement may be compensated.

While prevention of such displacements from eye movement are ensured by means of the invention by a rapid sequence of each of the three recordings, they must be taken into account during super-imposition of the recordings made at different focal planes and largely cleaned up, since the focal displacement and subsequent recording of each of the three images requires so much time that displacement from eye movements are unavoidable. Based on the invention, image-processing means are used here.

In a fundus camera based on the invention, the illumination pattern to be formed, the image recording device, and a fixation device of an accommodation device are preferably conjugated at the initial position before the depth scan, i.e., all are simultaneously focused on the retina. This can ensure that the eye is so accommodated that the illuminated area of the retina may be sharply formed on the image recording device. The setup used to perform a depth scan is so realized according to the invention that the displaceable lens is so positioned within the beam path that it alters only the focal position of pattern and image recording device, while the beam path and thereby the focus of the accommodation device remains unaltered. This prevents the accommodation of the eye working against the depth scan. (During the depth scan, the focal plane of the target is no longer conjugated with the focal planes of the illumination and of the recording.)

In another advantageous embodiment of the invention, the fixation target is formed as a planar object, while in conventional fundus cameras only a point-type object is positioned centrally along the optical axis. This makes possible steering within the eye to lateral positions during the recording in order to observe peripheral areas near the center area of the retina. For this, the fixation target may, for example, be formed as freely-steerable LED or OLED displays.

In another advantageous embodiment of the invention, the fundus camera is so implemented that photographs in different colors may be created, which is desirable for diverse diagnostic purposes. This may also be achieved in that the illumination device can emit light in different colors, such as is possible, for example, using an array of LED's of different colors. These have the advantage that they are capable of very quick switching, so that it is possible to make three recordings in different colors that may then be compared without allowing detraction caused by eye movement between recordings. It would also be possible to use a white light source and to introduce color filters of different colors into the illumination-beam path. A further possibility would be to use a color sensor for the image recording device in order thus to make recordings in specific different colors. This also makes it possible to realize fluorescence recordings using the fundus camera based on the invention. The important thing is that at least three recordings are made using one color, and are then combined.

In another advantageous embodiment of the invention, an iris camera is provided as a component of the fundus camera that observes the pupil and iris of the patient. Using such an iris camera, the entire fundus camera may be positioned in three dimensions relative to the eye. Adjustment of this camera to the eye along the three spatial dimensions is performed transversally using, for example, a fiber reticle to center the pupil and in the separation direction over the sharp image, for example to center the iris or the pupil edge.

For a full understanding of the present invention, reference should now be made to the following detailed description of the preferred embodiments of the invention as illustrated in the accompanying drawing.

DESCRIPTION OF THE PREFERRED EMBODIMENTS

Figure 1:
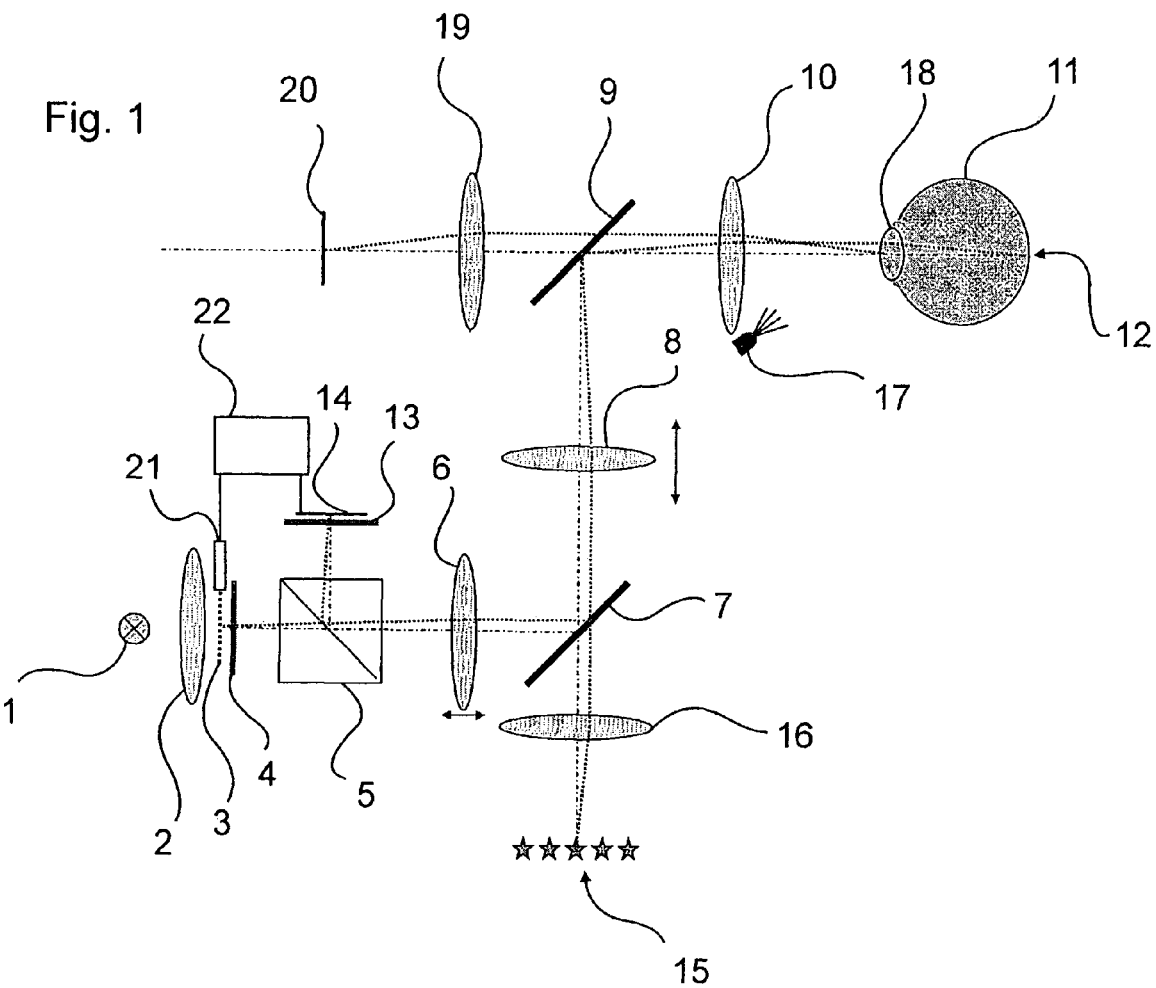
FIG. 1 shows schematically the structure of a fundus camera with patterned illumination in accordance with one preferred embodiment of the present invention.

The preferred embodiments of the present invention will now be described with reference to FIGS. 1 and 2 of drawings. Identical elements in the two Figures have been identified by the same reference numerals.

The fundus camera shown in the FIG. 1, based on the invention and suitable for high-resolution planar photographs, includes a light source 1 to illuminate the retina, whose light is formed via a condenser lens 2 and a mask 3 through a polarizer (e.g., a polarizing film) 4, through a polarizing beam splitter 5 and a projection lens 6 (this is the moveable lens for depth scan that relates only to illumination and projection), a dichroitic accommodation beam splitter 7 to split the accommodation beam path, a diopter lens 8 to match the camera to the individual vision deficiency of the patient, a dichroitic beam splitter 9 for the beam path of the iris camera and the objective lens 10 through the pupil of the eye 11. The mask 3, illuminated by the light source 1 via the condenser lens 2, or more specifically the dark-light pattern created by it, is formed against the retina 12. The light reflected or scattered back from the retina 12 is led back along the projection-beam path (that is identical to the illumination path) to the polarizing beam splitter 5 and from it via a recording-side polarizer (e.g., a polarizing film) 13 onto a recording sensor 14. The light emitted from a fixation target 15 via the accommodation beam splitter 7 and further focused by means of an additional projection lens 16 is coupled into the beam path and also passed to the retina 12 so that the fixation target is projected onto the retina. Further, a LED light source 17 is provided for diffuse illumination of the iris 18, whereby the light reflected from the iris 18 is decoupled from the beam path by means of a beam splitter 9 of the iris camera and projected by means of an iris-camera lens 19 onto an iris-camera sensor 20.

A suitable light source 1, for example, is a halogen lamp whose light for color photographs can be split using color filters (not shown) or a sensor 14 configured as a color sensor to obtain color photographs. LED's are just as suitable as a light source 1. These may be selected based on their spectra such that color-selective photographs, or color photographs in the case of white LED's with a color sensor, are possible. If one uses a color sensor as the sensor 14, one must ensure that the resolution of the sensor 14 is increased proportionally to the quantity of colors in order to ensure that a resolution of at least one mega pixel is available in each color photograph.

The light from the light source 1 is distributed evenly over a mask 3 by means of the condenser lens 2. In the advantageous embodiment example described here, the mask 3 is realized as a periodic line grid, and is connected with a piezo-motor, by means of which the line grid may be displaced by less than one grid unit. Because of this movement, the striped pattern formed along the projection beam path onto the retina 12 is displaced by less than one period. This makes it possible to take several photographs of an area of the retina 12 in sequence with the same striped pattern and to overlay them with an offset of less than one period. The images recorded at the sensor 14 are passed to a computer 22 in which they are processed into a single stripe-free combined photograph of the retina. The computer establishes a connection to a piezo-motor 21 so that the photographs at the sensor 14 may be correlated using the displacement of the motor 21. The illumination light passing through the mask 3 is polarized at the polarizer 4 so that only polarized light reaches the retina 12. This polarized light cannot reach the sensor 14 directly since another polarizer 13 is positioned before it whose polarization direction is perpendicular to that of the first polarizer 4. This prevents light that is reflected from one of the many optical elements or from the eye, which must be illuminated very strongly, from falling on the sensor 14, thereby distorting the recording of the retina 12. The light from the retina 12 to be recorded is largely depolarized upon reflection or back-scattering at the retina 12 so that it may at least partially pass through the polarizer 13 to reach the sensor 14. Polarization of illumination and projection light causes a certain degree of filtering of the very small component of useful light reflected or scattered back directly from the retina 12 from the large portion of interfering light caused by reflections from various components along the projection-beam path. This is the foundation for the assumption that the component of the beam reflecting or scattering back from the retina 12 is depolarized.

The projection lens 6 may be displaced along the beam path so that the focus of illumination and projection beam paths may be altered to the same degree. This makes it possible to sample various focal planes along the depth of the retina 12 and thus to create three planar recordings at different depths so that a depth scan of the retina 12 may be performed overall. The projection lens 6 is positioned before the beam splitter 7, by means of which the beam path of the fixation target 15 that serves to accommodate the eye is superimposed. This ensures that the displacement of the lens 6 along the accommodation-beam path has no effect, so that the accommodation of the eye is not altered while sampling of the depth of the retina 12 occurs by means of the displacement of the lens 6. Diopter adjustment to match the image formation of the camera with the individual vision defects of the patient's eye is performed using an additional displaceable lens 8, so that error-free focusing of the retina 12 is ensured. For this, it is necessary that the eye is accommodated to the fixation target 15, which is formed, for example, of flat LED's.

The additional LED light source 17 serves for the diffuse illumination of the iris 18 in order to provide a bright and easily-recognizable image of the iris for the positioning of the fundus camera with respect to the patient's eye. The light reflected or scattered back from the iris 18 is decoupled from the beam path by means of the beam splitter 9 of the iris camera and is projected by means of an iris-camera lens 19 onto an iris-camera sensor 20. The focal plane of the iris camera must be so adjusted that, upon sharp projection of the iris or especially of the pupil edge, the desired working distance of the fundus camera to the patient's eye is attained. Centering of the pupil image within the image field of the iris camera with the assistance of a fiber reticle if available positions the fundus camera such that the projection-beam path is directed optimally to the patient's eye for the fundus projection. The wavelength of the iris illumination is preferably so selected that first, it lies in different region of the spectrum than the spectrum of the illumination light for the fundus camera and the illumination of the fixation target, and second, it lies at the edge of the visible spectrum so that the overlay effect is minimal because of the reduced sensitivity or the eye. A preferred spectral range for the iris illumination is the near infra-red.

Figure 2:
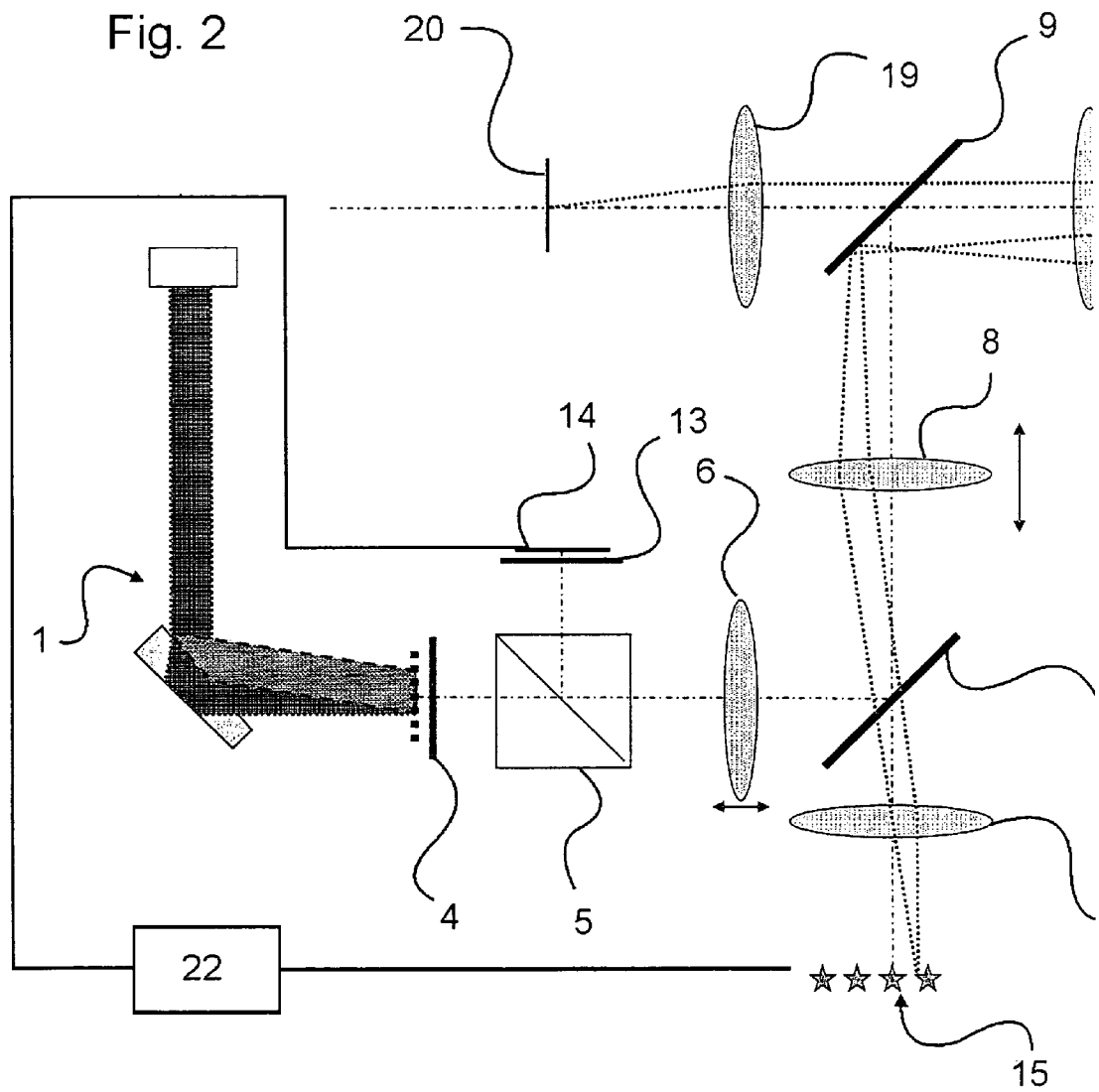
FIG. 2 shows schematically the structure of a fundus camera with patterned illumination in accordance with a second preferred embodiment of the present invention.

The fundus camera shown in FIG. 2, suitable for high-resolution surface recordings of the retina, also includes a light source 1 to illuminate the retina. It is represented here by an interferometer so that a line pattern is formed by the interference of coherent beams that may be projected against the eyeground. This projection is via a polarizing beam splitter 5 and a projecting lens 6, a dichroitic accommodation beam splitter 7 to split the accommodation-beam path, a Diopter lens 8 to match the camera to the individual vision defects of the patient, a dichroitic beam splitter 9 for the beam path of the iris camera and the objective lens 10 through the pupil of the eye 11 onto the retina 12. The light reflected from, or scattered back by, the retina 12 passes back along the projection beam path that is identical to the illumination beam path to the polarizing beam splitter, from which it is guided via an image-side polarizer (e.g., a polarizing film) 13 onto a recording sensor 14. The light emitted from the fixation target 15 and focused by an additional projection lens 16 is coupled in via the accommodation beam splitter 7 and also guided to the retina 12 so that the fixation target is projected onto the retina. Further, a LED light source 17 is provided for diffuse illumination of the iris 18 whereby the light reflected by the iris 18 is decoupled from the beam path by means of the beam splitter 9 of the iris camera, and is projected via an iris-camera lens onto an iris-camera sensor 20.

The line structure created from the light source 1 always remains in one place in this embodiment example. Displacement of the structure is by the movement of the eye 11. Because of this movement, the stripe pattern formed on the retina by the projection beam path is displaced by less than one period. This makes it possible to make several recordings of an area of the retina 12 in series using the same stripe pattern but displaced with respect to one another by less than one period. The images recorded at the sensor 14 are guided to a computer 22 in which they are processed into one single, stripe-free overall recording of the retina 12. A connection to the fixation target is established via the computer 22 so that the recordings at the sensor 14 may be correlated with the displacement of the fixation target. As soon as the fixation target 15 is displaced, the eye 11 moves in order to follow this displacement. This causes the stripe pattern to wander across the retina 12. Targeted displacement of the fixation target 15 may thus cause a targeted displacement of the stripe pattern. In this embodiment example, the displacement of the stripe pattern across the retina is caused not by a displacement of the pattern within the illumination unit, but rather by displacement of the retina 12, which here is caused by displacement of the fixation target 15.

All other components such as, for example, polarizers 4 and 13 and the widely-varying lenses fulfill the same functions in this embodiment as for the embodiment shown in FIG. 1.

There has thus been shown and described a novel fundus camera which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. Fundus camera for observing an eye, having an illumination device to illuminate an image field of the eyeground that is projected by means of a projection device onto an image recording device, whereby the illumination device and image recording device are positioned to be confocal, the improvement wherein the illumination device is so structured that a periodic light pattern is created against the eyeground within an illuminated image field and is provided with an offset medium to offset the pattern by less than one period, wherein the image recording device is coupled to an evaluation unit which combines a minimum of three recordings illuminated with offset patterns into a single image, and wherein a displaceable lens is positioned within a recording beam path and an illumination beam path in order to obtain a spatial photograph of the eyeground.

2. Fundus camera as defined in claim 1, wherein the offset medium has an offset time of less than 0.5 second.

3. Fundus camera as defined in claim 2, wherein the offset medium has an offset time of less than 0.1 second.

4. Fundus camera as defined in claim 2, wherein the offset medium includes an actuator.

5. Fundus camera as defined in claim 1, wherein the offset medium includes the eyeground.

6. Fundus camera as defined in claim 5, wherein the fundus camera includes a moveable fixation target, for controlling movement of the eyeground.

7. Fundus camera as defined in claim 6, wherein a movement device of the fixation target is coupled to the evaluation unit.

8. Fundus camera as defined in claim 1, wherein the offset medium includes means for creating a sine wave shaped, light intensity modulated, pattern against the eyeground, wherein said means produces periodicity along only one direction.

9. Fundus camera as defined in claim 1, wherein the image recording device has a resolution of at least one mega pixel.

10. Fundus camera as defined in claim 1, wherein optical elements are provided within beam paths of the camera for suppressing interfering reflections.

11. Fundus camera as defined in claim 10, wherein a polarizer is positioned within an illumination beam path and a polarizer is positioned within a recording beam path.

12. Fundus camera as defined in claim 11, wherein a polarizing beam splitter is positioned within the recording beam and illumination beam paths.

13. Fundus camera as defined in claim 10, wherein projecting optical elements are de-centered within the beam paths.

14. Fundus camera as defined in claim 10, wherein projecting optical elements are tilted within the beam paths.

15. Fundus camera as defined in claim 1, wherein the evaluation unit includes means for analyzing recordings made with different lens focus and, in response thereto, displacing the recordings with respect to one another so as to correct displacement of image information based on eye movements.

16. Fundus camera as defined in claim 15, further comprising an accommodation device having an accommodation beam path and a displaceable lens located outside the accommodation beam path.

17. Fundus camera as defined in claim 16, wherein the accommodation device includes a fixation target which is spatially expanded.

18. Fundus camera as defined in claim 1, wherein the illumination device is operative to selectively emit light of different wavelengths to create color-selective photographs.

19. Fundus camera as defined in claim 18, further comprising color filters inserted into an illumination beam path.

20. Fundus camera as defined in claim 1, wherein the image recording device includes a color sensor.

21. Fundus camera as defined in claim 1, further comprising an iris camera for aligning the fundus camera.

22. Fundus camera as defined in claim 8, wherein the means for creating a sine wave shaped, light intensity modulated pattern comprises a displaceable mask.

23. Fundus camera as defined in claim 22, wherein the means for creating a sine wave shaped, light intensity modulated pattern further includes a motor-powered actuator for displacing the mask.

24. Fundus camera as defined in claim 8, wherein the means for creating a sine wave shaped, light intensity modulated pattern comprises a interferometer.

* * * * *